United States Patent [19]

Vaughan et al.

[11] Patent Number: 4,832,824
[45] Date of Patent: May 23, 1989

[54] CATALYTIC REFORMING USING GROUP VIII NOBLE METAL HIGH SILICA FAUJASITES

[76] Inventors: David E. W. Vaughan, Box 596, R.D. 5, Flemington, N.J. 08822; Amal K. Ghosh, 25 Twin Oaks Rd., Bridgewater, N.J. 08807

[21] Appl. No.: 944,330

[22] Filed: Dec. 19, 1986

[51] Int. Cl.⁴ .................. C10G 35/06; C10G 15/393; C10G 2/52; C10G 5/13
[52] U.S. Cl. .................................. 208/138; 585/407; 585/419; 585/751
[58] Field of Search ................ 208/138; 585/419, 739, 585/751

[56] References Cited

U.S. PATENT DOCUMENTS

| | | | |
|---|---|---|---|
| 3,442,795 | 5/1969 | Kerr et al. | 208/120 |
| 3,475,345 | 10/1969 | Benesi | 502/74 |
| 3,591,488 | 7/1971 | Eberly, Jr. et al. | 208/111 |
| 3,640,681 | 2/1972 | Pickert | 423/328 |
| 3,673,267 | 6/1972 | Chen et al. | 502/374 |
| 3,714,029 | 1/1973 | Berry | 208/111 |
| 3,755,486 | 8/1973 | Oishi et al. | 585/419 |
| 3,953,320 | 4/1976 | Peck et al. | 208/111 |
| 3,980,550 | 9/1976 | Gorring et al. | 208/111 |
| 4,093,560 | 6/1978 | Kerr et al. | 423/328 |
| 4,148,713 | 4/1979 | Rollmann | 208/111 |
| 4,309,280 | 1/1982 | Rosinski et al. | 208/120 |
| 4,330,396 | 5/1982 | Miller | 208/136 |
| 4,347,394 | 8/1982 | Detz et al. | 585/419 |
| 4,431,746 | 2/1984 | Rollmann | 502/73 |
| 4,435,283 | 3/1984 | Buss et al. | 208/138 |
| 4,503,023 | 3/1985 | Breck et al. | 423/328 |
| 4,689,312 | 8/1987 | Ngocle | 585/739 |

FOREIGN PATENT DOCUMENTS 1506429 4/1978 United Kingdom .

Primary Examiner—Curtis R. Davis

[57] ABSTRACT

This process is for the reforming of (particularly; the aromatization of and isomerization of) alkanes to produce aromatics isonomal alkanes. Although the process and catalyst parameters can be adjusted to produce a majority of one or the other of the aromatic or isomerate products, the process is especially favorable for the production of a superior gasoline blending component having high octane blending values and containing significant amounts of both aromatics and branched paraffins. Only a small amount of cracking takes place. The process is catalytic and uses a high silica faujasite type zeolite, which contains a catalytic amount of at least one Group VIII noble metal, particularly platinum, within the pores of the zeolite.

21 Claims, 3 Drawing Sheets

CATALYTIC REFORMING USING GROUP VIII NOBLE METAL HIGH SILICA FAUJASITES

FIELD OF THE INVENTION

The instant invention relates to a process for the catalytic reforming of (particularly the aromatization of and isomerization of) normal alkanes to produce aromatics and iso alkanes. Although the process and catalyst parameters can be adjusted to produce a majority of one or the other of the aromatic or isomerate products, the process is especially suitable for the production of a superior gasoline blending component having high octane blending values and containing significant amounts of both aromatics and branched paraffins. Only a small amount of cracking takes place. The catalysts used are high silica faujasite zeolites, which contain a catalytic amount of at least one Group VIII noble metal, particularly platinum, within the pores of the zeolite.

BACKGROUND OF THE INVENTION

Since the advent of higher compression automobile and aircraft gasoline engines in the late 30's and 40's, the demand for higher octane gasoline has continually risen. For the past many years, this octane requirement has been supplied by the addition of various organolead compounds, notably tetraethyl lead (TEL), or other similar compounds, to mixtures of various hydrocarbons. However, because of the widespread use of catalytic convertors in removing undesirable components from the exhaust gases of automobiles (which convertors are poisoned by the use of lead in gasoline), other methods of improving motor gasoline octane became more important. One such method of improving the octane of a straight run-gasoline fraction is catalytic reforming.

Reforming may be practiced on naphtha feedstreams which have been desulfurized. Naphthas, "straight run" or otherwise, are generally obtained from simple distillation of a crude oil stream in a "pipe still". Straight run naphtha is typically highly paraffinic but may contain significant amounts of naphthenes and minor amounts of aromatics or olefins. In a typical reforming process, the reactions include dehydrogenation, isomerization, and hydrocracking. The dehydrogenation reactions typically will be the dehydroisomerization of alkylcyclopentanes to aromatics, the dehydrogenation of paraffins to olefins, the dehydrogenation of cyclohexanes and cyclohexenes to aromatics, and the dehydrocyclization of paraffins and olefins to aromatics. The aromatization of the n-paraffins to aromatics is generally considered to be the most important because of the high octane of the resulting aromatic product. The isomerization reactions include isomerization of n-paraffins to isoparaffins, the hydroisomerization of olefins to isoparaffins, and the isomerization of substituted aromatics. The hydrocracking reactions include the hydrocracking of paraffins and hydrodesulfurization if any sulfur compounds remain in the feedstock. On lighter naphtha streams, it is often desirable to avoid hydrocracking because of the low-carbon-number gaseous products which may result.

It is known that several catalysts are capable of reforming petroleum naphthas and hydrocarbons that boil in the gasoline boiling range. Examples of known catalysts useful for reforming include platinum (and optionally rhenium or iridium) on an alumina support, platinum on type X and Y zeolites, platinum on intermediate pore size zeolites as described in U.S. Pat. No. 4,347,394, platinum on cation exchanged type L zeolites, and palladium on mordenite.

As noted above, the typical reforming catalyst is a multi-functional catalyst which contains a metal hydrogenation-dehydrogenation component which is usually dispersed on the surface of a porous inorganic oxide support, notably alumina. Platinum has been widely commercially used in recent years in the production of reforming catalysts, and platinum on alumina catalysts have been commercially employed in refineries for the past few decades. In the last decade, additional metallic components, e.g., iridium, rhenium, tin and the like, have been added to platinum as promoters to further the activity, selectivity, or both, of the basic platinum catalyst. Some catalysts possess superior activity, or selectivity, or both, as contrasted with other catalysts. Platinum-rhenium catalysts, by way of example, possess high selectivity in contrast to platinum catalysts. Selectivity is generally defined as ability of the catalyst to produce yields of $C_{5}+$ liquid products with concurrent low production of normally gaseous hydrocarbons (i.e., methane) and coke. Multi-metallic catalysts containing platinum are discussed in length, see *Bimetallic Catalyst*, J. H. Sinfelt, John Wiley, New York, 1985.

In a typical reforming operation, one or a series of reactors, or a series of reaction zones, are employed. Typically, a series of reactors are employed, e.g., 3 or 4 reaction vessels, which constitute the heart of the reforming unit. Although there are cases where split feed operations are practiced, the typical reaction scheme involves a set of serial feed reactors.

It is known that the amount of coke produced in an operating run increases progressively from the leading reactor to subsequent reactors as a consequence of the different types of reactions that predominate in the several different reactors. The sum total of the reforming reactions occurs as a continuum between the first and last reactor of the series. The reactions which predominate among the several reactors differ principally upon the nature of the feed and at the temperature employed within the individual reactors. In the initial reaction zone, which is maintained at a relatively low temperature, the primary reaction involves dehydrogenation of naphthenes to produce aromatics. The isomerization of naphthenes, particularly $C_5+$ and $C_6$ naphthenes, also occurs to a considerable extent. Most of the other reforming reactions also occur, but only to a lesser extent. There is relatively little hydrocracking, and very little olefin or paraffin dehydrocyclization occurring in the first reactor. Typically, the temperature within the intermediate reactor zones is maintained at a somewhat higher level than in the first or lead reactor series. Primary reactions in these intermediate reactors involve the isomerization of naphthene and paraffins. Where, for instance, there are two reactors placed between the first and last reactor in series, the principal reaction in these middle two reactors involves isomerization of napthenes, normal paraffins and isoparaffins. Some dehydrogenation of napthenes may, and usually does, occur at least within the second of the four reactors. The amount of hydrocracking increases in the second reactor as does the gross amounts of olefin and paraffin dehydrocyclization.

The third reactor of the series is generally operated at a moderately higher temperature than the second reactor. The naphthene and paraffin isomerization reactions continue as the primary reaction in the reactor, but there is very little naphthene dehydrogenation. There is a further increase in paraffin dehydrocyclization, and more hydrocracking. In the final reaction zone, which is typically operated at the highest temperature of the series, paraffin dehydrocyclization, particularly dehydrocyclization of the short chain or $C_6$ and $C_7$ paraffins, is the primary reaction. The isomerization reactions continue and there is often more hydrocracking in this reactor than in any other reactor of the series.

Few processes are, however, capable of allowing adjustment of the aromatics to isoparaffin ratio by mere adjustment of the temperature or by selection of the $SiO_2/Al_2O_3$ ratio of the zeolite used in the catalyst.

The catalysts used in this process are zeolites having the faujasite structure, natural or synthetic, having a $SiO_2/Al_2O_3$ ratio of greater than about 6.0 and contain highly dispersed Group VIII noble metal, particularly platinum.

Other dealuminated zeolites are known. Typical processes suitable for dealuminating zeolites include the following:

- The U.S. patent to Kerr et al, U.S. Pat. No. 3,442,795, shows dealumination of various zeolites with complexing agents, notably EDTA.
- Eberly et al (U.S. Pat. No. 3,591,488) discloses a process for dealuminating zeolites (e.g., faujasites, mordenite, and erionite) using steam. The resulting materials are said (at column 5, lines 17 et seq) to be useful in a wide variety of hydrocarbon conversion reactions. Their use in hydrocracking is highlighted at column 5, lines 43 et seq.
- The U.S. patent to Pickert (U.S. Pat. No. 3,640,681) suggests the use of acetylacetonate to dealuminate partially a variety of large pore zeolites such as type X, type Y, type L and mordenite.
- Kerr et al (U.S. Pat. No. 4,093,560) teaches a method for dealuminating zeolites using an alkali or ammonium salt, preferably one of EDTA.
- Rollman (U.S. Pat. No. 4,431,746) also suggests using a complex containing transition metals of low or zero ion charge to dealuminate zeolite materials.
- Breck et al describes methods amounting to Al framework exchange using $(NH_4)_2SiF_6$ solutions (U.S. Pat. No. 4,503,023).

Dealuminated zeolites (or zeolites otherwise having high $SiO_2/Al_2O_3$ ratios) are used in a wide variety of hydrocarbon conversion operations:

| Patentee | U.S. Pat. No. | Metal | Zeolite | Process |
|---|---|---|---|---|
| Benesi | 3,475,345 | Pt | mordenite | paraffin isomerization |
| Chen et al | 3,673,267 | Group IB, VIB VIII | mordenite | paraffin isomerization |
| Peck et al | 3,953,320 | noble metals | mordenite | cracking isomerization |
| Goring et al | 3,980,550 | noble metals | ZSM-5 etc. | hydrodewaxing |
| Rollmann | 4,148,713 | pref. Pt | ZSM-5 etc. | alkylation, etc. |
| Rosinski et al | 4,309,280 | Re | ZSM-5 etc. | cracking |
| Miller | 4,330,396 | various | ZSM-5 etc. | "upgrading" |

The use of faujasite zeolites (sometimes of high $SiO_2/Al_2O_3$ ratio) to isomerize or aromatize various hydrocarbons has been shown.

U.S. Pat. No. 3,714,029 to Berry shows the use of zinc-substituted type Y zeolite to effectuate hydroisomerization of paraffins.

Buss et al (U.S. Pat. No. 4,435,283) teach the use of, inter alia, ziolites L, X and Y with Group VIII noble metal (particularly platinum) and alkaline earth metals as reforming catalysts.

A British patent (No. 1,506,429) to Best et al teaches the use of a zeolite Y, potentially of an enhanced $SiO_2/Al_2O_3$ ratio in a number of hydrocarbon conversion processes including reforming, isomerization and many others. The maximum disclosed $SiO_2/Al_2O_3$ ratio appears to be 5.4.

None of the cited prior art appears to suggest a process for paraffin isomerization and aromatization with low cracking using a high silica faujasite and containing a highly dispersed Group VIII noble metal, desirably platinum.

SUMMARY OF THE INVENTION

In accordance with the present invention, there is provided an improved catalytic reforming process the improvement which comprises employing, as the catalyst, a faujasite zeolite material having a $SiO_2/Al_2O_3$ ratio of about 10 to 80 and containing one or more Group VIII noble metals dispersed therein at a hydrogen to metal dispersion of about 0.1 to 1, as measured by hydrogen chemisorption.

In a preferred embodiment of the present invention the process is primarily aromatization of a paraffinic feed conducted at a temperature from about 450°–520° C., the faujasite material has a $SiO_2/Al_2O_3$ of about 30 to 50, and the noble metal is platinum.

In another preferred embodiment of the present invention, the process is primarily isomerization of normal and cycloparaffins conducted at a temperature of about 300° to 550° C., the faujasite material has a $SiO_2/Al_2O_3$ ratio of about 10 to 30, and the noble metal is platinum.

DETAILED DESCRIPTION OF THE INVENTION

Figure 1:
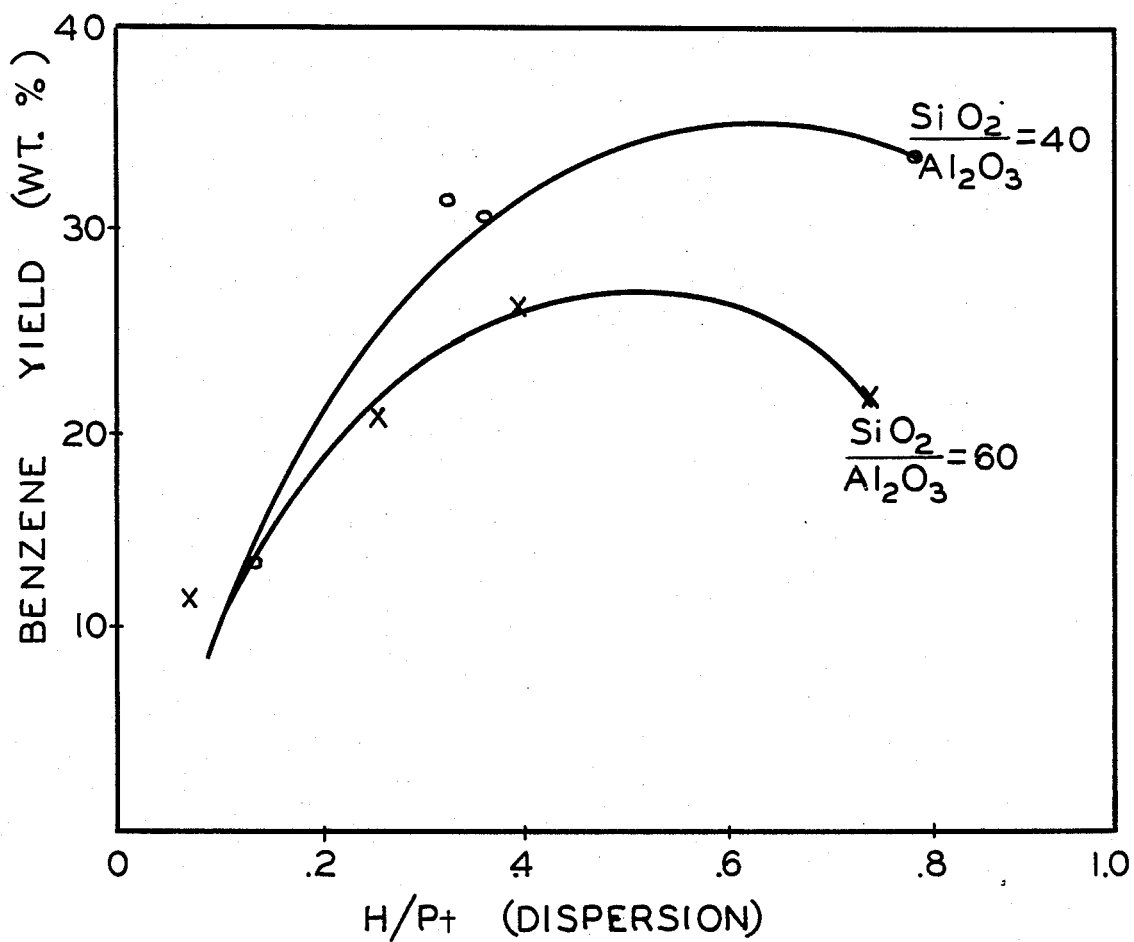
FIG. 1 shows a graph of benzene yield as a function of platinum dispersion (measured by hydrogen chemisorption) and $SiO_2/Al_2O_3$ ratios of the inventive catalyst.

As noted above, this invention is a catalytic reforming process for converting normal paraffinic hydrocarbons into isomeric paraffins, aromatic hydrocarbons, or both. The catalyst is derived from a faujasite zeolite having a relatively high $SiO_2/Al_2O_3$ ratio, e.g., at least 10, and which has a Group VIII metal, preferably platinum, finely dispersed therein.

By selection of the $SiO_2/Al_2O_3$ ratio, metal dispersion of the catalyst, and the temperature of the hydrocarbon conversion process, the process can be tailored to produce a stream containing the desired isomerate/aromatic makeup.

The Catalyst

As previously mentioned, the catalysts of the present invention are based upon a zeolite having a faujasite structure, preferably Y. Commercially available, as-synthesized, faujasites typically have $SiO_2/Al_2O_3$ ratios of no greater than about 5.0. The initial faujasite used herein may be treated using an acid/steam process to produce the material having a higher $SiO_2/Al_2O_3$ ratio. The acid used is desirably quite dilute, e.g., 0.1N to 6N, of an inorganic acid, preferably HCl. In any event, the zeolite may be slurried with the dilute acid for a suitable period of time, e.g., 1 to 5 hours and heated if desired. At the end of this step, the zeolite material is filtered, rinsed and dried. The zeolite is then steamed at a temperature of 600° to 850° C. This mild cycle of leaching and steaming may be repeated until the desired $SiO_2/Al_2O_3$ ratio is achieved. It is noted that this process minimizes the amount of detrital $Al_2O_3$ in the zeolite. Such materials may be effectively made by other processes, such as that disclosed in U.S. Pat. No. 4,503,023 to Breck et al.

A single cycle of 2N HCl leaching of a steamed ammonium exchanged type of faujasite (e.g. ELZ-20, Union Carbide Corp.) for 2 hours at 80°-100° C. and steaming 0.5 hours at 815° C. produces a $SiO_2/Alhd 2O_3$ ratio of 7 from a starting type Y material having a ratio of 4.8. This process may be repeated to achieve $SiO_2/Al_2O_3$ ratios in excess of 50.

The dealumination method used in producing the high silica faujasites of the present invention is not critical. The noted process allows the faujasite to retain more than 70% of its crystallinity (as reflected by its X-ray diffraction pattern) and retain a hexane sorption capacity of more than about 10% by weight.

The high silica faujasite materials used herein have a $SiO_2/Al_2O_3$ ratio of about 10 to 80. Those having $SiO_2/Al_2O_3$ ratios greater than about 80 have very little inherent activity in the hydrocarbon reactions discussed herein. Although any of the zeolite of this invention would be suitable for catalytic reforming, those having $SiO_2/Al_2O_3$ ratios from 30 to 50 are preferred. The predominant reactions in reforming, aromatization and isomerization, because of the bifunctional nature of the catalyst, can each be optimized by the judicious choice of $SiO_2$ to $Al_2O_3$ ratios. For example, when aromatization is the primary objective a $SiO_2/Al_2O_3$ ratio of 30 to 80 is used, preferably 30 to 50, more preferably 40±5. When isomerization is the primary objective the $SiO_2/Al_2O_3$ ratio is less than 40, preferably 15 to 40.

The Group VIII noble metals suitable for use herein are those metals from Group VIII of the Periodic Table of Elements which are selected from osmium, ruthenium, rhodium, iridium, palladium and platinum. Preferably, the metal is selected from platinum, rhodium and iridium, more preferably, platinum. The metals may be present in any combination desired. Rhenium, a Group VIIB metal, may also be present so long as at least one Group VIII noble metal is present.

The amount of Group VIII noble metal present in the catalysts of the present invention will be an effective amount and will depend, for example, on required catalyst activity, ease of uniform dispersion, and the crystal size of the zeolite. Channel size limits the effective catalyst loading since highly loaded crystals of zeolite could easily lead to pore plugging during operation as the noble metal agglomerates inside the channels. Generally, however, the level of metal present will range from about 0.1 to 6% by weight of the catalyst, preferably 0.1 to 3.5%, and more preferably 0.1 to 2.5%. Furthermore, the amount of metal present is generally from 0.1 to 2.0% by weight of the catalyst.

The Group VIII noble metals may be introduced into the zeolite by, for example, ion exchange, impregnation, carbonyl decomposition, adsorption from the gaseous phase, introduction during zeolite synthesis, and adsorption of metal vapor. The preferred technique is impregnation.

Since in the higher $SiO_2/Al_2O_3$ ranges of the zeolite, there are few cationic substitution sites, ion exchange is not typically very effective.

The catalyst may be bound in other supports. However, care should be taken to ensure that the supports do not interfere with the catalyst activity.

The Group VIII metal, or metals, may be introduced using an aqueous solution of chloroplatinic acid, chlorplatinious acid, tetraamineplatinum nitrate, denitrodiamineplatinum chloride, tetraamineplatinum chloride or tetraamineplatinum nitrate. The solution is simply introduced into the zeolite and dried (or calcined) at reasonable temperatures, e.g., 200° C. to 500° C.

The catalyst is then reduced in a hydrogen atmosphere at a temperature in the range of about 200° to about 500° C. for 0.5 to 6.0 hours. The reducing atmosphere need only contain more than about 15% hydrogen with the rest being a relatively inert gas such as nitrogen, argon, etc.

The dispersion of the Group VIII metal in the dispersed catalyst depends on such factors as: the concentration of the metal and the temperature of the calcination and reducing steps. Without wishing to be bound by this theory, it appears that catalysts having dispersion >0.4 are more active because the benzene yield from hexane is larger. Dispersion, the ratio of surface platinum atoms to all platinum atoms, may be measured by hydrogen chemisorption. Dispersion should be in the range of 0.1 to 1, preferably 0.4 to 1 for best aromatization and isomerization activity. FIG. 1 shows the relationship between product type and dispersion for a family of $SiO_2/Al_2O_3$ ratios.

The Process to conventional reforming of naphthas derived from petroleum, or other sources of hydrocarbons, and boiling in the range of about 70° to 215° C., but may also be employed to produce the corresponding products from any reactant organic compound containing at least six carbon atoms, including those which contain reactant functional groups. Examples of reactant compounds suitable for this purpose include paraffins, such as n-hexane, n-heptane, n-octane, n-nonane, etc. Preferred is a naphtha boiling in the range of 70° to 215° C. Preferred reactions include reforming, and aromatization of n-hexane to benzene, n-heptane to toluene, and n-octane to ethylbenzene and/or xylenes, n-Hexane may be present in the feed or produced by isomerization of methylpentanes and methylcyclopentane. The isomerization reaction includes the conversion of n-hexane to 2- or 3-methylpentane and dimethylbutanes; n-heptane to 2- and 3-methylhexane and various dimethyl pentanes; and similar highly branched isomerates.

Additional reactions where the catalyst may be employed advantageously include benzene production from streams such as light naphtha, i.e., a naphtha boiling between about 30° and 100° C., high octane gasoline production from naphtha or, light virgin naphtha, where the end point is between $C_7$ and $C_{12}$ inclusive.

The process described above may be carried out under general reforming conditions in the presence of hydrogen at a moderate pressure to thermodynamically favor the aromatization reaction. For traditional reforming of paraffins to aromatics, the temperature depends on the particular paraffin. For acceptable rates and selectivity, the preferred temperature ranges from about 400° to 550° C., more preferred is from about 450° to 520° C. at pressures of about 200 KPa to 5 MPa, preferably at pressures of about 500 KPa to 4 MPa. If the temperature is much below about 400° C., the yield of aromatic product is lower, and if the temperature substantially exceeds about 550° C., other reactions occur which also diminish the yield of desired product. The liquid hourly space velocity of this reforming reaction is preferably from about 0.5 to 20 w/w/hour, more preferably from 1 to 10 w/w/hour, and the $H_2$/reactant mole ratio is preferably from about 2 to 20, more preferably from about 4 to 10. For evaluation purpose, the LHSV was 50.

The dehydrocyclization reaction is generally carried out by injecting a feedstock charge in the presence of hydrogen gas into a reactor containing the catalyst.

Figure 2:
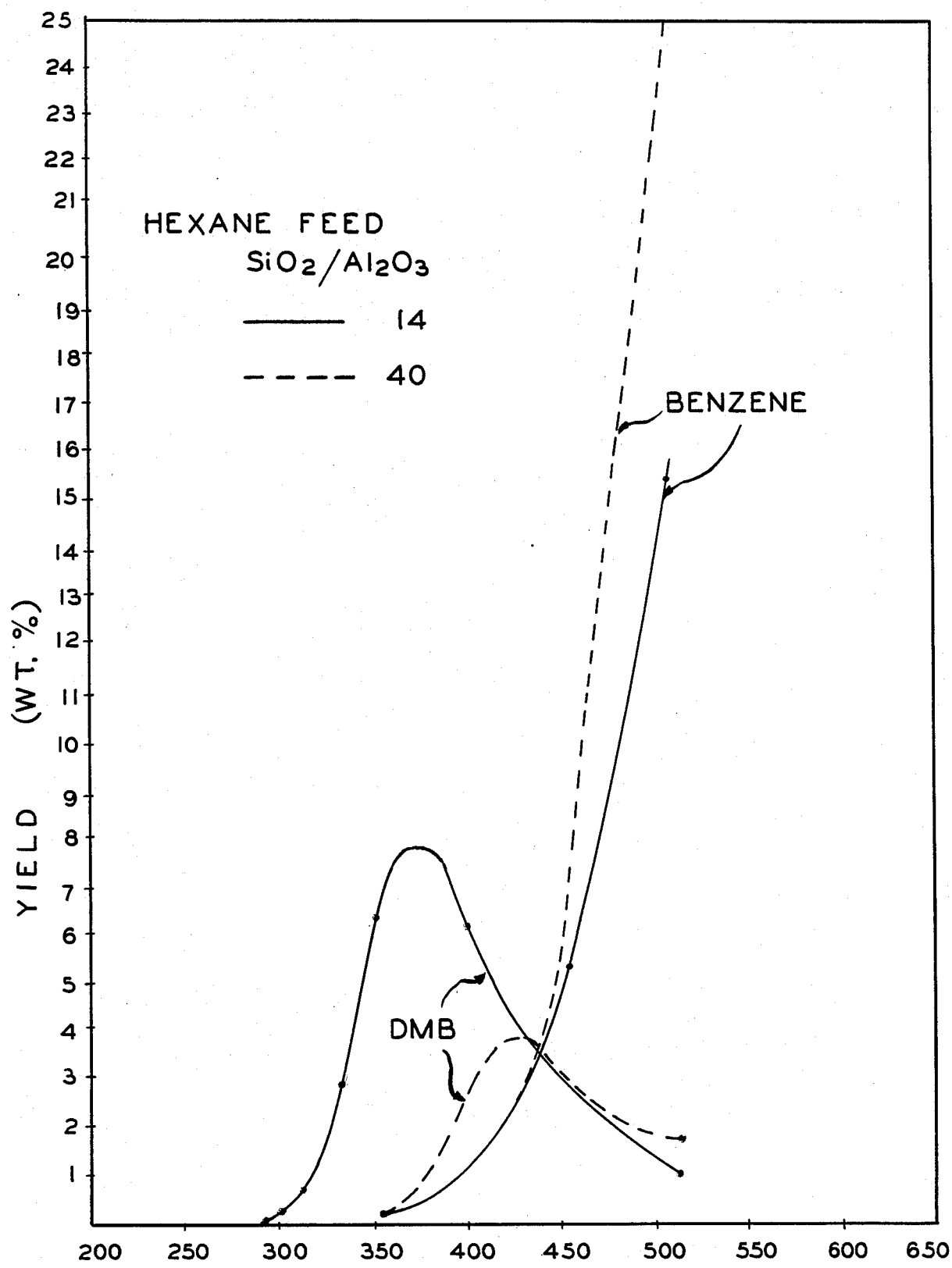
FIG. 2 shows a graph of isomerate dimethylbutane (DMB) and benzene (Bz) yield as a function of temperature using platinum-dealuminated zeolites of various $SiO_2/Al_2O_3$ ratios.
Figure 3:
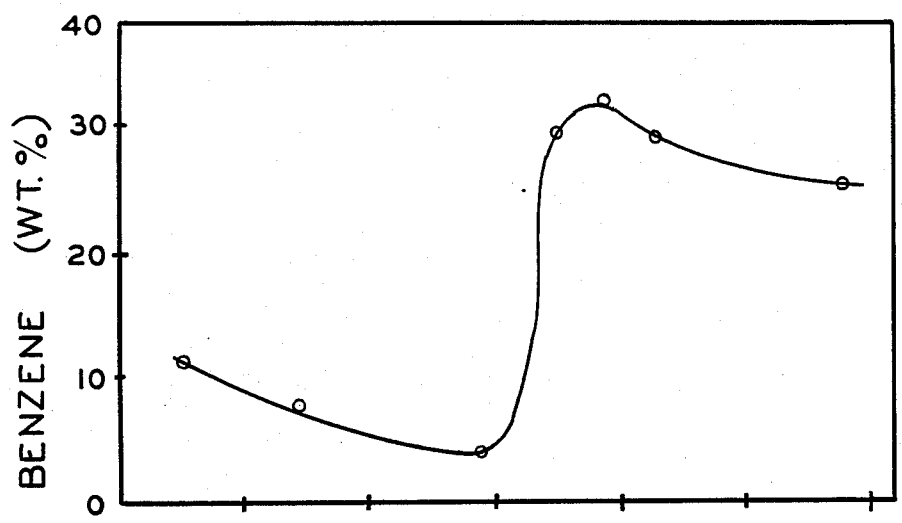
FIG. 3, 4 and 5 are graphs of benzene and isomerate yields at a particular set of reaction conditions as a function of $SiO_2/Al_2O_3$ ratio.
Figure 4:
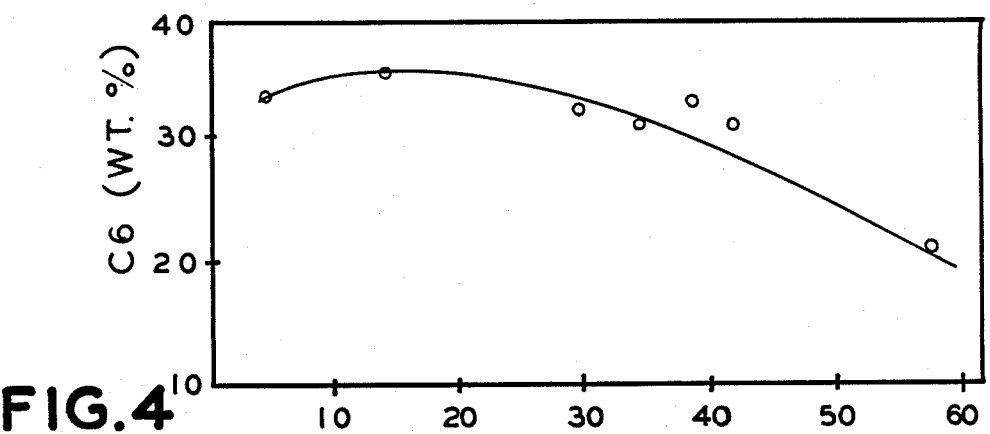
Figure 5:
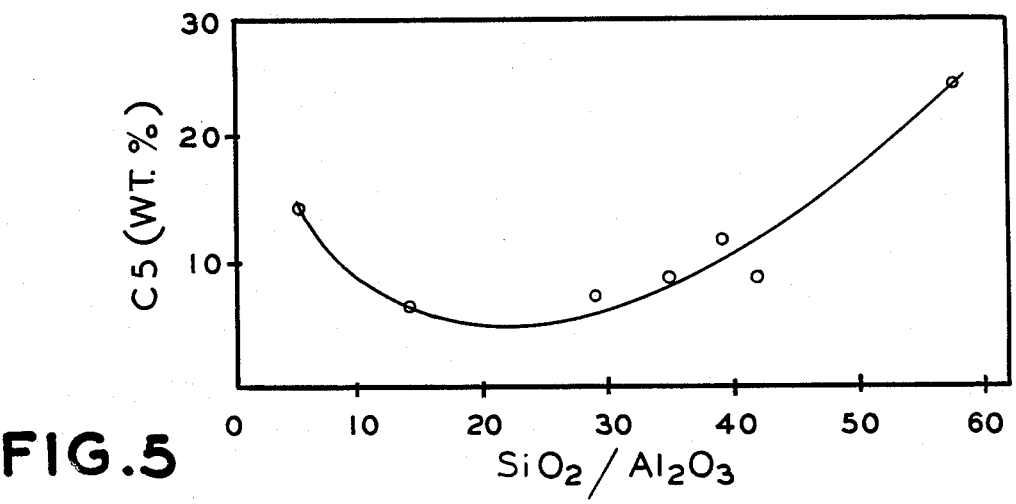

The isomerization reaction is carried out at the same pressure, LHSV, and $H_2$/reactant ratios but at generally lower temperatures. As is shown in FIG. 2, the isomerization reaction generally peaks (at a $SiO_2/Al_2O_3$ ratio of about 7) at about 375° C. Acceptable yields of isomerate may be found between about 340° C. and 410° C., preferably 360° to 400° C. However, if a mixture of isomerate and aromatics is desired, then higher temperatures are shown, e.g., between about 390° and 475° C. Mixtures of isomerate and aromatics are especially valuable as gasoline blending components.

At higher catalyst $SiO_2/Al_2O_3$ ratios, the desired temperatures are higher since the isomerization reaction is attenuated, the reactions to produce mixed products or aromatics are more feasible. FIG. 2 shows such a relationship.

It is within the scope of this invention to use catalysts made according to this invention to tailor the product mix attained. For instance, a mixture of a catalyst having a $SiO_2/Al_2O_3$ ratio of 30 and 60 would produce a mixture intermediate in composition.

EXAMPLES

Having explained the details of the process, below are some Examples of specific variations of the invention which illustrate the flexibility of the instant process. These Examples are not intended to be in any way limiting to the invention.

EXAMPLE 1

Catalyst Preparation

Dealumination of Faujasite

Several examples of LZ-20 faujasite (Union Carbide) were used as starting materials. The $SiO_2/Al_2O_3$ ratio of this material was <5. The "as received" zeolite was slurried with 2N HCl and refluxed at 80°-100° C. for two hours. The slurry was filtered, washed, and then reslurried with 2N HCl and refluxed again. After filtering and washing, the resulting cakes were placed in a drying oven for two hours and then into an 88% relative humidity dessicator overnight. The material was then placed in a furnace which had been preheated to 815° C. for 0.5 hours (steaming step). This sequence was repeated as necessary until the various desired $SiO_2/Al_2O_3$ ratios were attained.

Platinum Loading

The dealuminated faujasite samples were then dfied (350° C.) for one hour. Several stoichiometric amounts of Pt (as tetraammino platinum dichloride) were dissolved in predetermined amounts of distilled water (sufficient to give incipient wetness) and predetermined amounts of hot dealuminated faujasite were added and mixed completely. After aging and oven drying, the materials were calcined in air at 350° C. for three hours, then reduced in hydrogen.

EXAMPLES 2-9

These examples show the variation of benzene (Bz) yield with $SiO_2/Al_2O_3$ ratio and platinum dispersion. In each of these examples, a catalyst charge weighing 0.2 cm grams was introduced into a once through gas phase reactor. The operating conditions were: 510° C., $H_2$/hydrocarbon=6, pressure 100 psig, and space velocity=50 w/hr/w. The feedstock was hexane. Measurements were taken at 4 hours of operation.

TABLE 1

| | $SiO_2/Al_2O_3 = 40 \pm 4$ | | | |
|---|---|---|---|---|
| | Example | | | |
| | 1 | 2 | 3 | 4 |
| Dispersion (H/Pt) | 0.13 | 0.52 | 0.57 | 0.80 |
| Bz yield | 13.2 | 31.7 | 30.42 | 33.8 |
| $iC_6$ yield[1] | 35.6 | 31.3 | 33.68 | 35.0 |
| Bz selectivity | 20.6 | 42.9 | 40.4 | 40.9 |

[1] $iC_6$ = mixture of 2-methylpentane, 3-methylpentane, methylcyclopentane, and dimethylbutane.

TABLE 2

| | $SiO_2/Al_2O_3 = 60 \pm 4$ | | | | |
|---|---|---|---|---|---|
| | Example | | | | |
| | 5 | 6 | 7 | 8 | 9 |
| Dispersion (H/Pt) | 0.07 | 0.13 | 0.25 | 0.4 | 0.75 |
| Bz yield | 11.95 | 13.54 | 20.25 | 26.24 | 21.68 |
| $iC_6$ yield[1] | 18.22 | 18.65 | 18.65 | 29.35 | 21.58 |
| Bz selectivity | 18.9 | 21.35 | 38.73 | 35.57 | 31.27 |

These results are shown in FIG. 1.

EXAMPLES 10-21

This set of example demonstrates the variation of product type with temperature for catalysts having various $SiO_2/Al_2O_3$ ratios. The operating conditions (other than temperature) are the same as in Examples 2-9. Measurements are taken at 14 hours.

TABLE 3

| | $SiO_2/Al_2O_3 = 44$ H/Pt 0.57 | | | | | |
|---|---|---|---|---|---|---|
| | Ex. No. | | | | | |
| | 10 | 11 | 12 | 13 | 14 | 15 |
| T °C. | 310 | 350 | 410 | 450 | 490 | 510 |
| Bz yield | 0.25 | 0.16 | 1.31 | 7.15 | 20.66 | 30.99 |
| $iC_6$ yield | 0.43 | 1.24 | 9.9 | 26.77 | 35.31 | 33.24 |
| Bz select. | — | 4.8 | 9.63 | 18.62 | 31.74 | 42.48 |

These results are portrayed in FIG. 2.

TABLE

| | SiO$_2$/Al$_2$O$_3$ = 14 | | | | |
|---|---|---|---|---|---|
| | Ex. No. | | | | |
| | 16 | 17 | 18 | 19 | 20 |
| T °C. | 300 | 350 | 400 | 450 | 500 |
| Bz yield | — | 0.275 | 1.08 | 5.09 | 19.19 |
| iC$_6$ yield | 15.97 | 63.25 | 65.36 | 54.83 | 39.38 |
| Bz select. | — | 0.416 | 1.47 | 7.6 | 26.03 |

EXAMPLES 22-26

These examples show the variation of product type and yield with SiO$_2$/Al$_2$O$_3$ ratio. Other than the variables noted below, the reaction conditions are the same as in Examples 2-9.

TABLE 5

| | T = 510° C. | | | | | | |
|---|---|---|---|---|---|---|---|
| | Ex. No. | | | | | | |
| | 21 | 22 | 23 | 24 | 25 | 26 | 27 |
| SiO$_2$/Al$_2$O$_3$ | 5.6 | 14 | 36 | 40 | 60 | 44 | 30 |
| H/Pt | 0.71 | 0.98 | .52 | 0.8 | 0.75 | 0.57 | 0.3 |
| Bz yield | 12.16 | 8.33 | 31.17 | 33.82 | 26.40 | 30.42 | 4.24 |
| ic$_6$ yield | 34.06 | 36.81 | 31.62 | 35.04 | 21.58 | 33.68 | 32.74 |
| C$_5$- yield | 14.67 | 6.35 | 8.63 | 12.95 | 24.36 | 7.74 | 7.1 |

Having thus described the invention and examples, the invention has been thoroughly described. However, it should be made clear that this application is intended to cover those various changes and substitutions which may be made by those skilled in the art without departing from the spirit and scope of the invention.

We claim as our invention:

1. A process for reforming a naphtha feed stock utilizing a catalytic faujasite zeolite composition, which comprises contacting the feed stock at reforming conditions and in the presence of hydrogen with the catalytic zeolite having a faujasite structure and having a SiO$_2$/Al$_2$O$_3$ ratio between about 10 and 80 and containing a Group VIII noble metal dispersed therein so as to have a dispersion of hydrogen to metal of about 0.1 to 1, as measured by hydrogen chemisorption.

2. The process of claim 1 wherein the noble metal is platinum.

3. The process of claim 2 wherein the dispersion is between 0.4 and 1.

4. A process for aromatizing alkanes comprising the step of contacting the alkanes in the presence of hydrogen with a zeolitic catalyst having the structure of a faujasite and a SiO$_2$/Al$_2$O$_3$ ratio between 10 and 80 and containing a Group VIII noble metal catalyst dispersed therein so as to have a dispersion of hydrogen to noble metal at about 0.1 to 1, as measured by hydrogen chemisorption, at a temperature between 450° C. and 520° C. so as to aromatize at least a substantial portion of these alkanes.

5. The process of claim 4 wherein the Group VIII noble metal is platinum.

6. The process of claim 4 wherein the SiO$_2$/Al$_2$O$_3$ ratio is between 36 and 80.

7. The process of claim 4 wherein the dispersion is between 0.4 and 1.

8. The process of claim 4 wherein the alkanes comprise light naphtha.

9. The process of claim 4 wherein the alkanes comprise hexane.

10. A process for producing a mixed hydrocarbon stream containing isomeric alkanes and aromatics from alkanes comprising the step of contacting the alkanes in the presence of hydrogen with a zeolitic catalyst having the structure of a faujasite and a Si/Al ratio between 15 and 40 and containing a Group VIII noble metal catalyst dispersed therein so as to have a dispersion of hydrogen to metal of about 0.1 to 1, as measured by hydrogen chemisorption.

11. The process of claim 10 wherein the Group VIII noble metal is platinum.

12. The process of claim 10 wherein the Si/Al ratio is between 18 and 25.

13. The process of claim 10 wherein the dispersion is between 0.5 and 1 H/Pt.

14. The process of claim 10 wherein the alkanes comprise light naphtha.

15. The process of claim 10 wherein the alkanes comprise hexane.

16. A process for isomerizing alkanes comprising the step of contacting the alkanes in the presence of hydrogen with a zeolitic catalyst having the structure of a faujasite and a Si/Al ratio between 8 and 40 and containing a Group VIII noble metal catalyst dispersed therein so as to have a dispersion of hydrogen to metal of about 0.1 to 1, as measured by hydrogen chemisorption, at a temperature between 300° and 550° as to isomerize least a substantial portion of these alkanes.

17. The process of claim 16 wherein the Group VIII noble metal is platinum.

18. The process of claim 16 wherein the Si/Al ratio is between 18 and 25.

19. The process of claim 16 wherein the dispersion is between 0.5 and 1.

20. The process of claim 17 wherein the alkanes comprise light naphtha.

21. The process of claim 18 wherein the alkanes comprise hexane.

* * * * *

UNITED STATES PATENT AND TRADEMARK OFFICE
CERTIFICATE OF CORRECTION

PATENT NO. : 4,832,824

DATED : May 23, 1989

INVENTOR(S) : David E. W. Vaughan, et al.

It is certified that error appears in the above-identified patent and that said Letters Patent is hereby corrected as shown below:

On the title page, insert --[73] Assignee: Exxon Research and Engineering Company, Florham Park, N.J.--.

Signed and Sealed this

Twenty-ninth Day of May, 1990

Attest:

HARRY F. MANBECK, JR.

Attesting Officer

Commissioner of Patents and Trademarks